DEFENSIVE PUBLICATION

UNITED STATES PATENT OFFICE

Published at the request of the applicant or owner in accordance with the Notice of Dec. 16, 1969, 869 O.G. 687. The abstracts of Defensive Publication applications are identified by distinctly numbered series and are arranged chronologically. The heading of each abstract indicates the number of pages of specification, including claims and sheets of drawings contained in the application as originally filed. The files of these applications are available to the public for inspection and reproduction may be purchased for 30 cents a sheet.

Defensive Publication applications have not been examined as to the merits of alleged invention. The Patent Office makes no assertion as to the novelty of the disclosed subject matter.

PUBLISHED JULY 18, 1972

900 O.G. 820

T900,013

PROCESS FOR REMOVING METALLIC COLOR PRODUCING CONTAMINANTS FROM SOLUTIONS OF BIS(BETA-HYDROXYETHYL) TEREPHTHALATE IN ETHYLENE GLYCOL

Thomas G. Davis, 1542 Waverly Road 37664; David L. Nealy, 908 Afton St. 37660; and Jefferson W. Reynolds, 2121 E. Sevier St. 37664, all of Kingsport, Tenn.

Filed Nov. 2, 1971, Ser. No. 194,914
Int. Cl. C07c *69/82*
U.S. Cl. 260—475 PR
No Drawing. 8 Pages Specification

Metallic color producing contaminants present in bis-(beta-hydroxyethyl) terephthalate in solution in ethylene glycol may be removed from the monomer by contacting the solution at temperatures above about 140° C. with adsorbents typified by silica alumina, activated alumina, aluminum silicate $[Al_2(SiO_3)_3]$ alumina $(Al_2O_3)$ or activated carbon, and thereafter filtering the solution to remove the adsorbing agent or agents and the adsorbed metal contaminants.